United States Patent [19]

Lyman et al.

[11] Patent Number: 4,512,932

[45] Date of Patent: Apr. 23, 1985

[54] WATER REMOVAL OF TRIMETHYL PHOSPHATE FROM PHOSPHORUS CONTAINING PESTICIDES

[75] Inventors: Dale E. Lyman, Bumpass; James J. Anderson, Richmond, both of Va.

[73] Assignee: Mobil Oil Corporation, New York, N.Y.

[21] Appl. No.: 478,824

[22] Filed: Mar. 25, 1983

[51] Int. Cl.$^3$ ............................................. C07F 9/09
[52] U.S. Cl. .................................................. 260/990
[58] Field of Search ........................................ 260/990

[56] References Cited

U.S. PATENT DOCUMENTS

| | | | |
|---|---|---|---|
| 2,956,073 | 10/1960 | Whetstone et al. | 260/957 |
| 2,971,882 | 2/1961 | Ospenson et al. | 260/963 |
| 2,982,686 | 5/1961 | Whetstone et al. | 260/941 |
| 3,102,842 | 9/1963 | Phillips et al. | 260/957 |

OTHER PUBLICATIONS

Lange's Handbook of Chemistry, (1974), pp. 7-380-1, No. 6268.
The Merck Index, Tenth Ed., (1983), Nos. 3065, 2589, 6204, and 8675.

Primary Examiner—Anton H. Sutto
Attorney, Agent, or Firm—Alexander J. McKillop; Michael G. Gilman; Malcolm D. Keen

[57] ABSTRACT

A single of multi-step water extraction process is described for removing trimethyl phosphate (TMPO) from phosphorus containing pesticides having limited water solubility including 2,2-dichlorovinyl dimethyl phosphate (DDVP), dimethyl CIS-1-methyl-2(1-phenylethoxycarbonyl)vinyl phosphate, 1,2-dibromo-2,2-dichloroethyl dimethyl phosphate, and trans-2-chloro-1-(2,4,5-trichlorophenyl) vinyl dimethyl phosphate to a concentration of less than 1000 ppm. Methanol, dimethyl methylphosphonate, and dimethyl hydrogen phosphite are also removed from DDVP.

13 Claims, No Drawings

WATER REMOVAL OF TRIMETHYL PHOSPHATE FROM PHOSPHORUS CONTAINING PESTICIDES

BACKGROUND OF THE INVENTION

The present invention relates to a single or multi-step water extraction process for removing trimethyl phosphate (TMPO) from phosphorus containing pesticides having limited water solubility to produce a pesticide containing less than 1000 ppm TMPO.

A useful pesticide 2,2-dichlorovinyl dimethyl phosphate (DDVP), is disclosed in U.S. Pat. No. 2,956,073 wherein the DDVP is produced by reacting trimethyl phosphite (TMP) with chloral. The DDVP product often contains trimethyl phosphate (TMPO) which is an undesirable by-product. Other undesirable materials in the DDVP product include methanol, dimethyl methylphosphonate (DMMP), and dimethyl hydrogen phosphite (DMHP).

The present invention provides an economical and effective method for reducing the TMPO level below 1000 ppm for phosphorus containing pesticides by extraction with water. The pesticide may or may not be dissolved in a suitable solvent such as methylene chloride. In addition, the water extract removes other undesirable materials including methanol, DMMP, and DMHP.

SUMMARY OF THE INVENTION

In accordance with the present invention, a phosphorus containing pesticide manufactured from trimethyl phosphite having limited water solubility and containing trimethyl phosphate (TMPO) is contacted with water at a pesticide/water weight ratio of from about 1/10 to 10/1 in a first extraction zone thereby forming a primary pesticide raffinate reduced in TMPO and a water extract containing TMPO, and separating said primary pesticide raffinate from said extract. The pesticides treated are selected from the group consisting of 2,2-dichlorovinyl dimethyl phosphate (DDVP), dimethyl CIS-1-methyl-2(1-phenylethoxycarbonyl)vinyl phosphate, 1,2-dibromo-2,2-dichloroethyl dimethyl phosphate, and trans-2-chloro-1-(2,4,5-trichlorophenyl)vinyl dimethyl phosphate. The extracting step is conducted at a temperature from about 5° C. to 95° C. and a pressure of from about 0.1 to 10 atmospheres. A plurality of extraction steps using the same extracting conditions are conducted until the pesticide raffinate contains less than 1000 ppm TMPO. Thereafter, the pesticide raffinate product containing less than 1000 ppm TMPO is water stripped at 70° C. and 20 mmHg pressure. If the pesticide initially contains less than 2200 ppm TMPO, only one water extraction step is required to reduce the TMPO concentration to less than 1000 ppm. The water also extracts methanol, dimethyl methylphosphate and dimethyl hydrogen phosphite.

DESCRIPTION OF THE PREFERRED EMBODIMENT

Phosphorus containing pesticides manufactured from trimethyl phosphite contain trimethyl phosphate (TMPO) as an undesirable contaminant. The phosphorus containing pesticides treated in accordance with this invention for removal of TMPO have limited water solubility and include 2,2-dichlorovinyl dimethyl phosphate (DDVP), dimethyl CIS-1-methyl-2(1-phenylethoxycarbonyl)vinyl phosphate, 1,2-dibromo-2,2-dichloroethyl dimethyl phosphate, and trans-2-chloro-1-(2,4,5-trichlorophenyl)vinyl dimethyl phosphate. These pesticides may also contain other impurities such as methanol, dimethyl methylphosphonate (DMMP), and dimethyl hydrogen phosphite (DMHP).

In treating DDVP, the liquid DDVP is contacted with water having a pH within the range of 2.0 to 11.0 and preferably 3.0 to 7.0. Contacting is carried out at a DDVP/H$_2$O weight ratio within the range of 1/10 to 10/1, a temperature within the range of 5° C. to 95° C., preferably 20° C. to 30° C., and a pressure within the range of 0.1 to 10 atmospheres, preferably atmospheric pressure. The DDVP and water may be countercurrently contacted in an extraction zone or introduced into an extraction zone and agitated. An extract phase comprising TMPO and water is withdrawn from the upper portion of the extraction zone and is suitably treated for discharge as a waste stream. The extract phase also contains methanol, DMMP, and DMHP. The DDVP raffinate phase reduced in TMPO is removed from the lower portion of the extraction zone and passed to a plurality of separate extraction zones using the same extraction conditions of pesticide/water weight ratio, temperature and pressure as in the first extraction zone until the DDVP raffinate contains less than 1000 ppm TMPO. For example, if 3 extraction stages are necessary, the primary raffinate is passed to the second extractor and the secondary raffinate from the second extractor is passed to the third extractor from which the desired raffinate is recovered. The number of extraction stages will vary depending upon the initial concentration of TMPO in the DDVP. Often, only one extraction is necessary. For example, if the TMPO level in DDVP is less than 2200 ppm, only one extraction stage is required to reduce the TMPO to less than 1000 ppm. The final DDVP raffinate containing less than 1000 ppm TMPO is recovered and stripped of residual water at 70° C. and 20 mmHg pressure. The stripped water may be recovered and recycled to the extraction zone. Water immiscible solvents such as methylene chloride, ethylene chloride, or xylene may be used in this process advantageously for the removal of residual water from the purified DDVP product via a low boiling azeotrope.

In another embodiment of the present invention, the pesticide may be dissolved in methylene chloride prior to extraction of TMPO. The solutions useful in the process of this invention contain methylene chloride within the range of about 10% to 200% by weight of the pesticide. In extracting TMPO from these solutions, the extracting conditions are the same as previously described.

In order to more fully illustrate the process of the present invention, the following specific examples, which in no sense limit the invention, are presented.

EXAMPLE

Equal weights of water and DDVP containing 8800 ppm TMPO and 27,600 ppm DMMP were shaken for one minute and allowed to stand in separating funnels. The contacting was conducted at ambient temperature and atmospheric pressure. The primary DDPV raffinate bottom phase was drawn off and analyzed for TMPO, DDMP, and DDVP loss determined by (% DDVP×wt initial)−(% DDVP×wt final) divided by % DDVP×wt initial. The primary DDVP raffinate analysis showed 2200 ppm TMPO, 4,600 ppm DMMP, 96.3% DDVP and a DDVP loss of 1.10%. Equal weights of water and the recovered primary DDVP raffinate were contacted using the same procedure as previously described and the recovered secondary DDVP raffinate was water stripped at 70° C. and 20 mmHg pressure, ±2 mm for one hour. Analysis of the secondary DDVP raffinate showed 300 ppm TMPO, 300 ppm DMMP, 97.6% DDVP, and a DDVP loss of 2.70%.

From the foregoing specification one skilled in the art can readily ascertain the essential features of this invention and without departing from the spirit and scope thereof can adapt it to various diverse applications. It is our intention and desire that our invention be limited only by those restrictions or limitations as are contained in the claims appended immediately hereinafter below.

What is claimed is:

1. A method for treating a liquid phosphorus containing pesticide manufactured from trimethyl phosphite having limited water solubility and containing trimethyl phosphate (TMPO) comprising extracting the TMPO by contacting said pesticide with water until the pesticide raffinate contains less than 1000 ppm TMPO.

2. The method of claim 1 wherein the pesticide is selected from the group consisting of 2,2-dichlorovinyl dimethyl phosphate (DDVP), dimethyl CIS-1-methyl-2(1-phenylethoxycarbonyl)vinyl phosphate, 1,2-dibromo-2,2-dichloroethyl dimethyl phosphate, and trans-2-chloro-1-(2,4,5-trichlorophenyl)vinyl dimethyl phosphate.

3. The method of claim 2 wherein the pesticide is DDVP and the extraction is performed at a pesticide/water weight ratio of from about 1/10 to 10/1, a temperature of from about 5° C. to 95° C., and a pressure from about 0.1 to 10 atmospheres.

4. The method of claim 3 wherein the temperature is from about 20° C. to 30° C.

5. The method of claim 3 wherein the pressure is atmospheric pressure.

6. The method of claim 3 wherein the water extractant has a pH range of from about 2.0 to 11.0.

7. The method of claim 6 wherein the water extractant has a pH range of from about 3.0 to 7.0.

8. The method of claim 6 wherein the water extractant has a pH of 7.0.

9. The method of claim 1 wherein the recovered pesticide raffinate product is stripped to effect separation of water therefrom.

10. The method of claim 9 wherein the stripping is effected at a temperature of about 70° C. and a pressure of about 20 mmHg.

11. The method of claim 1 wherein the pesticide is dissolved in methylene chloride prior to extraction wherein the amount of methylene chloride is within the range of about 10% to 200% by weight of the pesticide.

12. The method of claim 1 wherein the pesticide contains less than 2200 ppm TMPO and the extraction of TMPO from the pesticide to a concentration less than 1000 ppm is effected in one stage.

13. The method of claim 1 wherein the pesticide is contacted with water in a plurality of extraction stages until the pesticide raffinate contains less than 1000 ppm TMPO.

* * * * *